United States Patent [19]

Manning et al.

[11] Patent Number: 4,544,663
[45] Date of Patent: Oct. 1, 1985

[54] INDOLAMINE DERIVATIVES AS ANTI-FERTILITY AGENTS

[75] Inventors: Robert E. Manning, Mt. Lakes; Jeffrey Nadelson, Denville, both of N.J.

[73] Assignee: Sandoz, Inc., E. Hanover, N.J.

[21] Appl. No.: 607,667

[22] Filed: May 7, 1984

[51] Int. Cl.[4] .................... A61K 31/40; A61K 31/42
[52] U.S. Cl. .................................. 514/378; 514/412; 514/414; 514/419; 514/841
[58] Field of Search ................................. 424/272, 274

[56] References Cited

U.S. PATENT DOCUMENTS

| 4,336,378 | 6/1982 | Brand et al. | 544/137 |
| 4,336,379 | 6/1982 | Brand et al. | 544/137 |
| 4,421,752 | 12/1983 | Brand et al. | 424/248.4 |

Primary Examiner—Leonard Schenkman
Attorney, Agent, or Firm—Gerald D. Sharkin; Robert S. Honor; Thomas O. McGovern

[57] ABSTRACT

This disclosure relates to the aspermatogenesis activity of
(a) compounds of the formula:

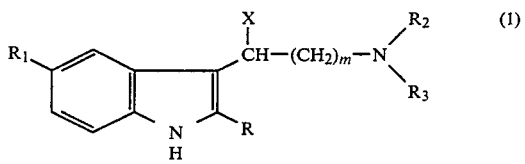

where
m is an integer from 1 to 4
X represents hydrogen or —OH
R represents Ar,

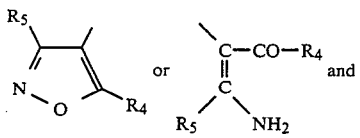

Ar represents

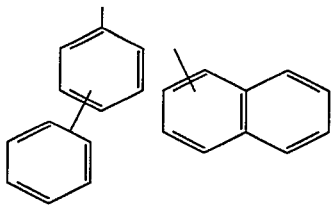

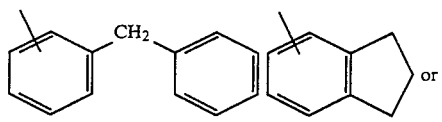

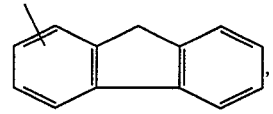

$R_1$ represents hydrogen, fluoro, chloro, lower alkyl or lower alkoxy,
$R_2$ and $R_3$ each, independently, represent lower alkyl, or
$R_2$ and $R_3$ together with N represent

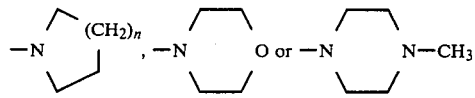

wherein
n is 1, 2 or 3,
$R_4$ represents hydrogen or lower alkyl, and
$R_5$ represents hydrogen or lower alkyl, unsubstituted phenyl or phenyl mono- or di-substituted with fluoro, chloro, lower alkyl or lower alkoxy, or
(b) compounds of the formula:

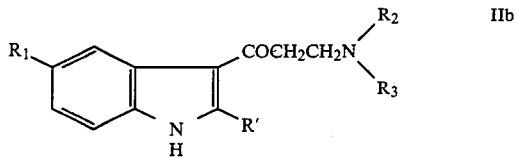

where R' is Ar or

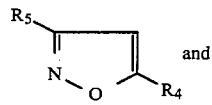

and

Ar, $R_1$, $R_2$, $R_3$, $R_4$ and $R_5$ are as defined above, or a pharmaceutically acceptable acid addition salt thereof.

21 Claims, No Drawings

INDOLAMINE DERIVATIVES AS ANTI-FERTILITY AGENTS

This invention relates to the aspermatogenesis activity of 3-aminoalkyl indolamine derivatives. More particularly, this invention concerns the use of 3-aminoalkyl substituted indolamines as male anti-fertility agents.

The active agents with which this invention is concerned are referred to as the compounds of formula (I) and may be represented (a) by the following structural formula:

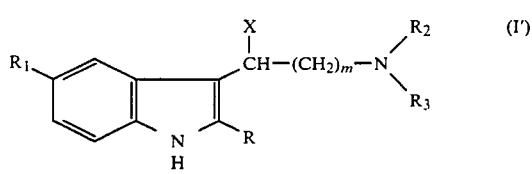

where
m is an integer from 1 to 4
X represents hydrogen or —OH,
R represents Ar,

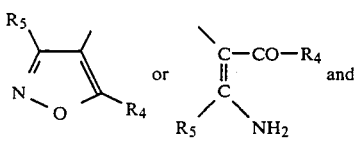

Ar represents

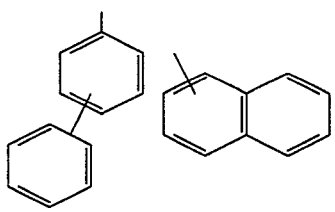

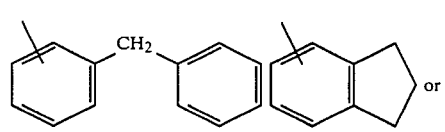

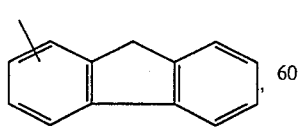

wherein
$R_1$ represents hydrogen, fluoro, chloro, lower alkyl, i.e., alkyl having 1 to 4 carbon atoms, e.g., methyl, ethyl, isopropyl and the like, or lower alkoxy, i.e., alkoxy having 1 to 4 carbon atoms, e.g., methoxy, ethoxy, and the like, and $R_2$ and $R_3$ each, independently, represent lower alkyl as defined above, or $R_2$ and $R_3$ together with N represent

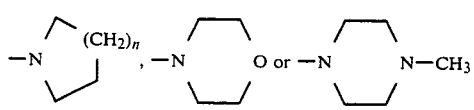

wherein
n is 1, 2 or 3, and
$R_4$ represents hydrogen or lower alkyl as defined above, and
$R_5$ represents hydrogen, lower alkyl as defined above or unsubstituted phenyl or phenyl substituted with fluoro, chloro, lower alkyl as defined above or lower alkoxy as defined above or (b) by the following structural formula:

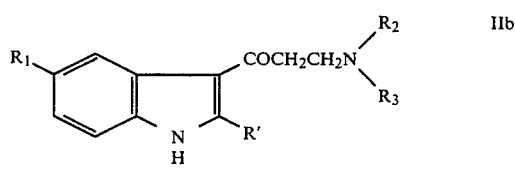

where R' is Ar or

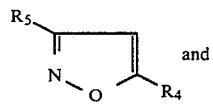

Ar, $R_1$, $R_2$, $R_3$, $R_4$ and $R_5$ are as defined above, or a pharmaceutically acceptable acid addition salt thereof.

The compound of formula (I') in which R is the aminoalkenone group

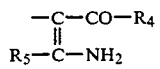

can exist in the following tautomeric forms

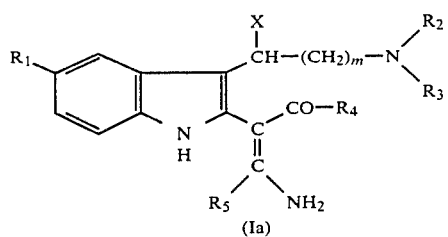
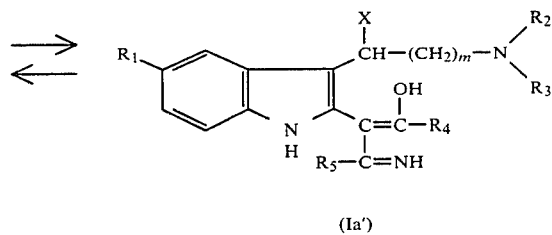

The compounds can also exist in the following geometrical forms:

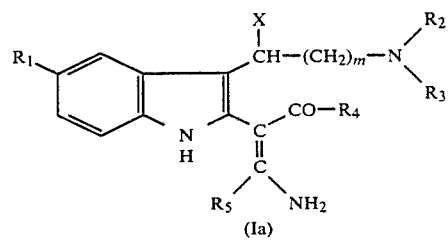
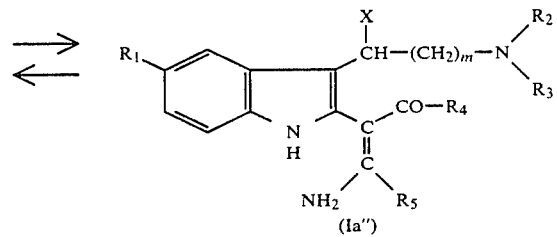

All of the tautomeric forms and geometrical isomers and their pharmaceutically acceptable salts are included within the scope of the presently claimed invention.

It will also be appreciated that the compounds of formula (I') in which X is OH may exist in the form of optically active isomers, which can be separated and recovered by conventional techniques, and that such isomeric forms are included within the scope of this invention.

The compounds of formula (I) are known and can be prepared by methods described in the literature. The compounds of formula (I) in which R is an isoxazolyl group and their preparation are disclosed in U.S. patent application Ser. No. 196,784, filed Oct. 14, 1980, which issued as U.S. Pat. No. 4,336,378 on June 22, 1982, Ser. No. 245,188, filed Mar. 18, 1981, which issued as U.S. Pat. No. 4,336,379 on June 22, 1982 and Ser. No. 251,068 filed Apr. 6, 1981, which issued as U.S. Pat. No. 4,336,391 on June 22, 1982. The compounds of formula (I) in which R is Ar or

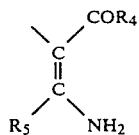

and their preparation are disclosed in British Patent Application No. 8309729 which published as No. 2,119,372 on Nov. 16, 1983.

Preferred compounds of formula I are those in which m is 1 and X is hydroxy, especially those in which X is hydroxy, R is isoxazole, $R_1$ is hydrogen or fluoro and $R_2$, $R_3$, $R_4$ and $R_5$ are lower alkyl and their pharmaceutically acceptable acid addition salts. The especially preferred compound is α-(dimethylaminomethyl)-2-(3-ethyl-5-methyl-4-isoxazolyl)-1H-indole-3-methanol. Also of interest are α-(diethylaminomethyl)-2-(3-ethyl-5-methyl-4-isoxazolyl)-1H-indole-3-methanol; α-(pyrrolidinomethyl)-2-(3-ethyl-5-methyl-4-isoxazolyl)-1H-indole-3-methanol; α-(dimethylaminomethyl)-2-(5-ethyl-3-methyl-4-isoxazolyl)-1H-indole-3-methanol; α-(dimethylaminomethyl)-5-fluoro-2-(3,5-dimethyl-4-isoxazolyl)-1H-indole-3-methanol; 2-(2-naphthyl)-3-[2-(N,N-dimethylamino)ethyl]-1H-indole; 2-(3-ethyl-5-methyl-4-isoxazolyl)-3-(3-dimethylaminopropyl)indole; 4-amino-3-[3-(2-dimethylamino-1-hydroxyethyl)-1H-indol-2-yl]-3-hexen-2-one; and 3-dimethylamino-1-[2-(3-ethyl-5-methyl-4-isoxazolyl)-1H-indole-3-yl]-1-propanone.

The compounds of formula (I) may be administered as such or in the form of their non-toxic pharmaceutically acceptable acid addition salts. Such salts possess the same order of activity as the free base and are readily prepared by reacting the compound with a pharmaceutically acceptable acid by conventional techniques. Representative of the inorganic salts are the hydrochloride, hydrobromide, hydroiodide, phosphate (including hydrogen phosphate), metaphosphate, and sulfate (including hydrogen sulfate). Representative examples of the organic salts are the acetate, maleate, fumarate and the like. The compounds of formula (I) may also be isolated in the form of salts with bases, e.g., alkali metal salts such as sodium or potassium salts. The use of such salt forms as male anti-fertility agents also form part of the invention.

As disclosed above, the compounds of formula (I) are useful because they possess aspermatogenesis activity in mammals. In particular, the compounds of formula (I) are useful as male anti-fertility agents, as indicated by the reduction or cessation of spermatogenic activity in adult Beagle dogs. Adult Beagle dogs in groups of two are given orally 12, 36 and 120 milligrams per kilograms per day (mg/kg/day) of the test compound for 14 to 16 consecutive days. Semen samples are collected from all dogs one week before testing is commenced and weekly thereafter to determine microscopically the sperm counts essentially in accordance with the procedure of Kolmer, et al (Approved Laboratory Technique, 5th Ed., (286, 1959). Upon necropsy, the dogs are sacrificed; and the testes and epididymis from all animals are collected and preserved in 10% neutral buffered formalin until examined histopathologically for various stages of aspermatogenesis.

When the above test is carried out with α-(dimethylaminomethyl)-2-(3-ethyl-5-methyl-4-isoxazolyl)-1H-indole-3-methanol, spermatogenesis is observed after 4 days at 120 mg/kg/day. Significantly reduced spermatogenesis is found after 14 days in the dogs given 12 mg/kg/day of test compound, and aspermatogenesis is observed in the dogs given 36 and 120 mg/kg/day. Two dogs similarly given 120 mg/kg/day of the above compound for 14 days are observed for an additional 120 days after administration of the compound is stopped. By day 85, the viable sperm count in the two dogs increases substantially; and by day 106, both dogs have counts within normal limits which remained normal for the remainder of the 120-day period. Upon necropsy, histopathological examination reveals no evidence of testicular damage or aspermatogenesis.

Equivalent results are obtained when the compound used in the test is:

(1) α-(dimethylaminomethyl)-2-(3-ethyl-4-isoxazolyl)-1H-indole-3-methanol,
(2) α-(dimethylaminomethyl)-2-(3,5-diethyl-4-isoxazolyl)-1H-indole-3-methanol,
(3) α-(dimethylaminomethyl)-2-(3-ethyl-5-isopropyl-4-isoxazolyl)-1H-indole-3-methanol,
(4) α-(dimethylaminomethyl)-2-(3-ethyl-5-t-butyl-4-isoxazolyl)-1H-indole-3-methanol,
(5) α-(dimethylaminomethyl)-2-(3,5-dimethyl-4-isoxazolyl)-1H-indole-3-methanol,
(6) α-(dimethylaminomethyl)-2-(5-methyl-4-isoxazolyl)-1H-indole-3-methanol,
(7) α-(dimethylaminomethyl)-2-(5-methyl-3-propyl-4-isoxazolyl)-1H-indole-3-methanol,
(8) α-(dimethylaminomethyl)-2-(5-methyl-3-t-butyl-4-isoxazolyl)-1H-indole-3-methanol,
(9) α-(dimethylaminomethyl)-2-(5-ethyl-3-methyl-4-isoxazolyl)-1H-indole-3-methanol,
(10) α-(dimethylaminomethyl)-2-(3-isopropyl-5-methyl-4-isoxazolyl)-1H-indole-3-methanol,
(11) α-(dimethylaminomethyl)-5-fluoro-2-(3-ethyl-5-methyl-4-isoxazolyl)-1H-indole-3-methanol,
(12) α-(dimethylaminomethyl)-5-methyl-2-(3-ethyl-5-methyl-4-isoxazolyl)-1H-indole-3-methanol,
(13) α-(dimethylaminomethyl)-5-methoxy-2-(3-ethyl-5-methyl-4-isoxazolyl)-1H-indole-3-methanol,
(14) α-(diethylaminomethyl)-2-(3-ethyl-5-methyl-4-isoxazolyl)-1H-indole-3-methanol,
(15) α-(morpholinomethyl)-2-(3-ethyl-5-methyl-4-isoxazolyl)-1H-indole-3-methanol,
(16) α-(pyrrolidinomethyl)-2-(3-ethyl-5-methyl-4-isoxazolyl)-1H-indole-3-methanol,
(17) α-(piperidinomethyl)-2-(3-ethyl-5-methyl-4-isoxazolyl)-1H-indole-3-methanol,
(18) α-(pyrrolidinomethyl)-5-fluoro-2-(3-ethyl-5-methyl-4-isoxazolyl)-1H-indole-3-methanol,
(19) α-(dimethylaminomethyl)-5-fluoro-2-(3,5-dimethyl-4-isoxazolyl)-1H-indole-3-methanol,
(20) α-(dimethylaminomethyl)-5-fluoro-2-(3-methyl-5-ethyl-4-isoxazolyl)-1H-indole-3-methanol,
(21) α-(pyrrolidinomethyl)-5-fluoro-2-(5-ethyl-3-methyl-4-isoxazolyl)-1H-indole-3-methanol,
(22) α-(pyrrolidinomethyl)-5-fluoro-2-(3,5-dimethyl-4-isoxazolyl)-1H-indole-3-methanol,
(23) 2-(5-methyl-3-phenyl-4-isoxazolyl)-3-(dimethylaminoethyl)-indole,
(24) 5-fluoro-2-(5-methyl-3-phenyl-4-isoxazolyl)-3-(dimethylaminoethyl)-indole,
(25) 5-methyl-2-(5-methyl-3-phenyl-4-isoxazolyl)-3-(dimethylaminoethyl)-indole,
(26) 5-methoxy-2-(5-methyl-3-phenyl-4-isoxazolyl)-3-(dimethylaminoethyl)-indole,
(27) 2-(5-methyl-3-phenyl-4-isoxazolyl)-3-(morpholinoethyl)-indole,
(28) 2-(5-methyl-3-phenyl-4-isoxazolyl)-3-(piperidinoethyl)-indole,
(29) 2-(5-methyl-3-phenyl-4-isoxazolyl)-3-(4-methylpiperazinoethyl)-indole,
(30) 2-(2-naphthyl)-3-[2-(N,N-dimethylamino)ethyl]-1H-indole,
(31) 2-(o-biphenyl)-3-[2-(N,N-dimethylamino)ethyl]-1H-indole;
(32) 2-(p-biphenyl)-3-[2-(N,N-dimethylamino)ethyl]-1H-indole;
(33) 2-(o-benzylphenyl)-3-[2-(N,N-dimethylamino)ethyl]-1H-indole;
(34) 2-(2-fluorenyl)-3-[2-(N,N-dimethylamino)ethyl]-1H-indole;
(35) 2-(5-indanyl)-3-[2-(N,N-dimethylamino)ethyl]-1H-indole;
(36) 5-fluoro-2-(2-naphthyl)-3-[2-(N,N-dimethylamino)ethyl-1H-indole;
(37) 5-methyl-2-(2-naphthyl)-3-[2-(N,N-dimethylamino)ethyl-1H-indole;
(38) 5-methoxy-2-(2-naphthyl)-3-[2-(N,N-dimethylamino)ethyl-1H-indole;
(39) 2-(5-methyl-3-phenyl-4-isoxazolyl)-3-[2-(N,N-dimethylamino)ethyl]-1H-indole;
(40) 2-(2-naphthyl)-3-(2-pyrrolidinoethyl)-1H-indole;
(41) 2-(2-naphthyl)-3-(2-piperidinoethyl)-1H-indole;
(42) 2-(2-naphthyl)-3-(2-morpholinoethyl)-1H-indole,
(43) 2-(2-naphthyl)-3-[1-hydroxy-2-(N,N-dimethylamino)ethyl]-1H-indole;
(44) 2-(o-biphenyl)-3-[1-hydroxy-2-(N,N-dimethylamino)ethyl]-1H-indole;
(45) 2-(p-biphenyl)-3-[1-hydroxy-2-(N,N-dimethylamino)ethyl]-1H-indole;
(46) 2-(o-benzylphenyl)-3-[1-hydroxy-2-(N,N-dimethylamino)ethyl]-1H-indole;
(47) 2-(2-fluorenyl)-3-[1-hydroxy-2-(N,N-dimethylamino)ethyl]-1H-indole;
(48) 2-(5-indanyl)-3-[1-hydroxy-2-(N,N-dimethylamino)-ethyl]-1H-indole;
(49) 5-fluoro-2-(2-naphthyl)-3-[1-hydroxy-2-(N,N-dimethylamino)ethyl]-1H-indole;
(50) 5-methyl-2-(2-naphthyl)-3-[1-hydroxy-2-(N,N-dimethylamino)ethyl]-1H-indole;
(51) 5-methoxy-2-(2-naphthyl)-3-[1-hydroxy-2-(N,N-dimethylamino)ethyl]-1H-indole;
(52) 2-(5-methyl-3-phenyl-4-isoxazolyl)-3-[1-hydroxy-2-(N,N-dimethylamino)ethyl]-1H-indole;
(53) 2-(2-naphthyl)-3-(1-hydroxy-2-pyrrolidinoethyl)-1H-indole;
(54) 2-(2-naphthyl)-3-(1-hydroxy-2-piperidinoethyl)-1H-indole;
(55) 2-(2-naphthyl)-3-(1-hydroxy-2-morpholinoethyl)-1H-indole;
(56) 2-(3-ethyl-5-methyl-4-isoxazolyl)-3-(3-dimethylaminopropyl)-indole;
(57) 2-(5-methyl-3-phenyl-4-isoxazolyl)-3-(3-dimethylaminopropyl)-indole;
(58) 5-fluoro-2-(5-methyl-3-phenyl-4-isoxazolyl)-3-(3-dimethylaminopropyl)-indole;
(59) 2-(2-naphthyl)-3-(3-dimethylaminopropyl)-indole;
(60) 2-(o-biphenyl)-3-(3-dimethylaminopropyl)-indole;
(61) 3-dimethylamino-1-[2-(3-ethyl-5-methyl-4-isoxazolyl)-1H-indole-3-yl]-1-propanol;
(62) 3-dimethylamino-1-[2-(5-methyl-3-phenyl-4-isoxazolyl)-1H-indol-3-yl]-1-propanol;
(63) 3-dimethylamino-1-[5-fluoro-2-(5-methyl-3-phenyl-4-isoxazolyl)-1H-indol-3-yl]-1-propanol;

(64) 3-dimethylamino-1-[2-(2-naphthyl)-1H-indol-3-yl]-1-propanol;
(65) 3-dimethylamino-1-[2-(o-biphenyl)-1H-indol-3-yl]-1-propanol;
(66) 2-(3-ethyl-5-methyl-4-isoxazolyl)-3-(4-dimethylaminobutyl)-indole;
(67) 4-amino-3-[(2-dimethylamino-1-hydroxyethyl)-1H-indol-2-yl]-3-hexen-2-one;
(68) 4-amino-3-[3-(2-dimethylamino-1-hydroxyethyl)-1H-indol-2-yl]-4-phenyl-3-buten-2-one;
(69) 4-amino-3-(5-fluoro-3-[(2-dimethylamino-1-hydroxyethyl)-1H-indol-2-yl]-3-hexen-2-one;
(70) 4-amino-3-[5-methyl-3-(2-dimethylamino-1-hydroxyethyl)-1H-indol-2-yl]-3-hexen-2-one;
(71) 4-amino-3-[5-methoxy-3-(2-dimethylamino-1-hydroxyethyl)-1H-indole-2-yl]-3-hexen-2-one;
(72) 4-amino-3-[3-(2-morpholino-1-hydroxyethyl)-1H-indol-2-yl]-3-hexen-2-one;
(73) 4-amino-3-[3-(2-pyrrolidino-1-hydroxyethyl)-1H-indol-2-yl]-3-hexen-2-one;
(74) 4-amino-3-[3-(2-piperidino-1-hydroxyethyl)-1H-indol-2-yl]-3-hexen-2-one;
(75) 4-amino-3-[3-(3-dimethylaminopropyl-1H-indol-2-yl]-4-phenyl-3-buten-2-one;
(76) 4-amino-3-[3-(2-dimethylaminoethyl)-1H-indol-2-yl]-3-hexen-2-one;
(77) 4-amino-3-[3-(2-dimethylaminoethyl)-1H-indol-2-yl]-4-phenyl-3-buten-2-one;
(78) 4-amino-3-[3-(2-dimethylaminoethyl)-5-fluoro-1H-indol-2-yl)-4-phenyl-3-buten-2-one;
(79) 4-amino-3-[3-(2-dimethylaminoethyl)-5-methyl-1H-indol-2-yl]-4-phenyl-3-buten-2-one;
(80) 4-amino-3-[3-(2-dimethylaminoethyl)-5-methoxy-1H-indol-2-yl]-4-phenyl-3-buten-2-one;
(81) 4-amino-3-[3-(2-morpholinoethyl)-1H-indol-2-yl]-4-phenyl-3-buten-2-one;
(82) 4-amino-3-[3-(2-piperidinoethyl)-1H-indol-2-yl]-4-phenyl-3-buten-2-one;
(83) 4-amino-3-[3-(3-dimethylaminopropyl)-1H-indol-2-yl]-3-hexen-2-one;
(84) 4-amino-3-[3-(4-dimethylaminobutyl)-1H-indol-2-yl]-3-hexen-2-one;
(85) 3-dimethylamino-1-[2-(3-ethyl-5-methyl-4-isoxazolyl)-1H-indol-3-yl]-1-propanone;
(86) 3-dimethylamino-1-[2-(5-methyl-3-phenyl-4-isoxazolyl)-1H-indol-3-yl]-1-propanone;
(87) 3-dimethylamino-1-[5-fluoro-2-(5-methyl-3-phenyl-4-isoxazolyl)-1H-indol-3-yl]-1-propanone;
(88) 3-dimethylamino-1-[2-(2-naphthyl)-1H-indol-3-yl]-1-propanone; or
(89) 3-dimethylamino-1-[2-(o-biphenyl)-1H-indol-3-yl]-1-propanone.

For use as anti-fertility agents, the compounds of formula (I) and their non-toxic, pharmaceutically acceptable salts may be administered orally as such or orally and parenterally with conventional pharmaceutical carriers. They may be administered orally in such forms as tablets, dispersible powders, granules, capsules, syrups and elixirs, and parenterally as solutions, e.g., a sterile injectable aqueous solution. The compositions for oral use may contain one or more conventional adjuvants, such as sweetening agents, flavoring agents, coloring agents and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose, and talc, granulating and disintegrating agents, e.g., starch and alginic acid, binding agents, e.g., magnesium stearate, stearic acid and talc. The tablets may be coated by known techniques to delay disintegration and absorption in the gastro-intestinal tract and thereby provide a sustained action over a longer period. Similarly, suspension, syrups and elixirs may contain the active ingredient in admixture with any of the conventional excipients utilized in the preparation of such compositions, e.g., suspending agents such as methylcellulose, tragacanth and sodium alginate; wetting agents such as lecithin, polyoxyethylene stearate and polyoxyethylene sorbitan monooleate; and preservatives such as ethyl p-hydroxybenzoate. Capsules may contain the active ingredient alone or admixed with an inert solid diluent, e.g., calcium carbonate, calcium phosphate and kaolin. The injectable compositions are formulated by methods well known in the art. These pharmaceutical preparations contain from about 0.5 to about 90 percent by weight based on the final composition of the active ingredient in combination with the carrier or adjuvant.

The anti-fertility effective dosage of the compounds of formula (I) employed in producing aspermatogenesis will vary depending on the particular compound employed, and the severity of the condition being treated. However, in general, satisfactory results are obtained when the compounds of formula (I) are administered at a daily dosage of from about 12 milligrams to about 120 milligrams per kilogram of animal body weight, preferably given in divided doses one or two times a day, or in sustained release form. For most large mammals, the total daily dosage is from about 200 to about 2000 milligrams, preferably 500 to about 1000 milligrams. Dosage forms suitable for internal use comprise from about 100 to about 1000 milligrams of the active compound in intimate admixture with a solid or liquid pharmaceutically acceptable carrier or diluent.

The preferred pharmaceutical compositions from the standpoint of preparation and ease of administration are solid compositions, particularly hard-filled capsules and tablets containing from about 250 to about 500 milligrams of the active ingredient.

TABLETS AND CAPSULES SUITABLE FOR ORAL ADMINISTRATION

Tablets and capsules containing the ingredients indicated below may be prepared by conventional techniques and are useful as an anti-fertility agent at a dose of one or two tablets or capsules two to four times a day.

| Ingredients | Weight (mg.) | |
| --- | --- | --- |
| | tablet | Capsule |
| α-(dimethylaminomethyl)-2-(3-ethyl-5-methyl-4-isoazolyl)-1H—indole-3-methanol | 250 | 250 |
| Tragacanth | 10 | — |
| Lactose | 197.5 | 250 |
| Corn Starch | 25 | — |
| Talcum | 15 | — |
| Magnesium Stearate | 2.5 | — |
| Total | 500 | 500 |

Similarly, tablets and capsules useful as anti-fertility agents can be prepared using compounds 1 through 89 above in place of the above compound at the same dosage level.

What is claimed is:

1. A method of inducing aspermatogenesis in male mammals requiring anti-fertility treatment which comprises administering to the mammal an anti-fertility therapeutically effective amount of
   (a) a compound of the formula:

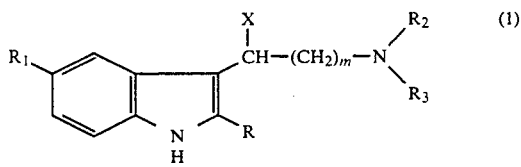

where
   m is an integer from 1 to 4
   X represents hydrogen or —OH
   R represents Ar,

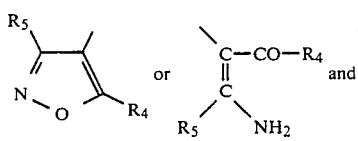

Ar represents

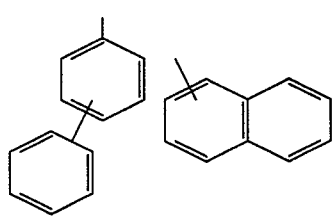

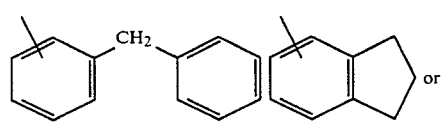

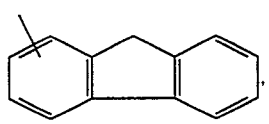

$R_1$ represents hydrogen, fluoro, chloro, lower alkyl or lower alkoxy,
$R_2$ and $R_3$ each, independently, represent lower alkyl, or
$R_2$ and $R_3$ together with N represent

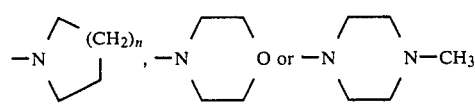

wherein
   n is 1, 2 or 3,
   $R_4$ represents hydrogen or lower alkyl, and
   $R_5$ represents hydrogen or lower alkyl, unsubstituted phenyl or phenyl mono- or di-substituted with fluoro, chloro, lower alkyl or lower alkoxy, or
(b) a compound of the formula:

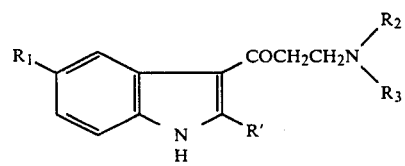

where R' is Ar or

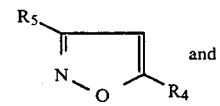

and

Ar, $R_1$, $R_2$, $R_3$, $R_4$ and $R_5$ are as defined above, or a pharmaceutically acceptable acid addition salt thereof.

2. A method according to claim 1 in which 200 to 2000 milligrams of the compound are administered daily.
3. A method according to claim 1 in which 500 to 1000 milligrams of the compound are administered daily.
4. A method according to claim 1 in which 100 to 1000 milligrams of the compound are administered per unit dose.
5. A method according to claim 1 in which 250 to 500 milligrams of the compound are administered per unit dose.
6. A method according to claim 1 in which X is hydroxy.
7. A method according to claim 1 in which m is 1.
8. A method according to claim 1 in which R is

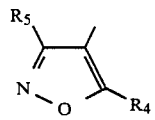

where $R_4$ and $R_5$ are as defined in claim 1.

9. A method according to claim 1 in which R is

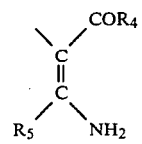

where $R_4$ and $R_5$ are as defined in claim 1.

10. A method according to claim 1 in which R is

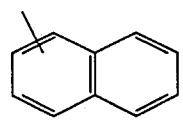

11. A method according to claim 1 in which $R_2$ and $R_3$ are lower alkyl.
12. A method according to claim 1 in which $R_4$ and $R_5$ are lower alkyl.
13. A method according to claim 1 in which $R_1$ is fluoro.

14. A method according to claim 6 in which $R_1$ is hydrogen or fluoro and $R_3$, $R_4$, $R_5$ and $R_6$ are lower alkyl.

15. The method according to claim 1 in which the compound is α-(dimethylaminomethyl)-2-(3-ethyl-5-methyl-4-isoxazolyl)-1H-indole-3-methanol, or a pharmaceutically acceptable salt thereof.

16. The method according to claim 1 in which the compound is α-(pyrrolidinomethyl)-2-(3-ethyl-5-methyl-4-isoxazolyl)-1H-indole-3-methanol, or a pharmaceutically acceptable salt thereof.

17. The method according to claim 1 in which the compound is α-(dimethylaminomethyl)-5-fluoro-2-(3,5-dimethyl-4-isoxazolyl)-1H-indole-3-methanol, or a pharmaceutically acceptable salt thereof.

18. The method according to claim 1 in which the compound is 2-(2-naphthyl)-3-[2-(N,N-dimethylamino)ethyl]-1H-indole or a pharmaceutically acceptable salt thereof.

19. The method according to claim 1 in which the compound is 2-(3-ethyl-5-methyl-4-isoxazolyl)-3-(3-dimethylaminopropyl)-indole or a pharmaceutically acceptable salt thereof.

20. The method according to claim 1 in which the compound is 4-amino-3-[3-(2-dimethylamino-1-hydroxyethyl)-1H-indol-2-yl]-3-hexen-2-one or a pharmaceutically acceptable salt thereof.

21. The method according to claim 1 in which the compound is α-(dimethylaminomethyl)-2-(5-ethyl-3-methyl-4-isoxazolyl)-1H-indole-3-methanol or 3-dimethylamino-1-[2-(3-ethyl-5-methyl-4-isoxazolyl)-1H-indol-3-yl]-1-propanone, or a pharmaceutically acceptable salt thereof.

* * * * *